(12) United States Patent
O'Brien et al.

(10) Patent No.: US 6,291,663 B1
(45) Date of Patent: Sep. 18, 2001

(54) TADG-12: A NOVEL TRANSMEMBRANE SERINE PROTEASE OVEREXPRESSED IN A OVARIAN CARCINOMA

(75) Inventors: Timothy J. O'Brien; Lowell J. Underwood, both of Little Rock, AR (US)

(73) Assignee: Board of Trustees of the University of Arkansas, Little Rock, AR (US)

( * ) Notice: Subject to any disclaimer, the term of this patent is extended or adjusted under 35 U.S.C. 154(b) by 0 days.

(21) Appl. No.: 09/261,416

(22) Filed: Mar. 3, 1999

(51) Int. Cl.[7] .............................. C07H 21/04; C07K 1/00; G01N 33/48

(52) U.S. Cl. ....................... 536/23.5; 536/23.5; 536/24.5; 530/350; 530/395; 436/64

(58) Field of Search ................................. 536/23, 5, 24.5; 530/350, 395; 436/64

(56) References Cited

PUBLICATIONS

Tanimoto, et al, "Cloning and expression of TADG–15, a novel serine protease expressed in ovarian cancer" Proceeding of the American Association for Cancer Research, vol. 39, p. 648, 1998.*

O'Brien et al, "Cloning and expression of TADG–15, a novel serine protease expressed in ovarian cancer.", Tumor Biology, Suppl 2, p. 33, 1998.*

* cited by examiner

*Primary Examiner*—Anthony C. Caputa
*Assistant Examiner*—Karen A. Canella
(74) *Attorney, Agent, or Firm*—Benjamin Aaron Adler

(57) ABSTRACT

The present invention provides a DNA encoding a TADG-12 protein selected from the group consisting of: (a) isolated DNA which encodes a TADG-12 protein; (b) isolated DNA which hybridizes to isolated DNA of (a) above and which encodes a TADG-12 protein; and (c) isolated DNA differing from the isolated DNAs of (a) and (b) above in codon sequence due to the degeneracy of the genetic code, and which encodes a TADG-12 protein. Also provided is a vector capable of expressing the DNA of the present invention adapted for expression in a recombinant cell and regulatory elements necessary for expression of the DNA in the cell.

8 Claims, 11 Drawing Sheets

```
      251
Prom  CGGVLIHPLW  VLTAAHCKKP  NLQV.....FL  GKHNLRQRES  SQEQSSVVRA
Try1  CGGSLINEQW  VVSAGHCYKS  RIQV.....RL  GEHNIEVLEG  NEQFINAAKI
Scce  CGGVLVNERW  VLTAAHCKMN  EYTV.....HL  GSDTLGDRRA  ..QRIKASKS
Heps  CGGSLLSGDW  VLTAAHCFPE  RNRVLSRWRV  FAGAVAQASP  HGLQLGVQAV
T12   CGGSVITPLW  IITAAHCVYD  LYLPKS.WTI  QVGLVSLLDN  PAPSHLVEKI 301                                                    350
Prom  VIHPDY....  ..DAASHDQD  IMLLRLARPA  KLSELIQPLP  LERDCS..AN
Try1  IRHPQY....  ..DRKTLNND  IMLIKLSSRA  VINARVSTIS  LPTAPP..AT
Scce  FRHPGY....  ..STQTHVND  LMLVKLNSQA  RLSSMVKKVR  LPSRCE..PP
Scce  FRHPGY....  ..STQTHVND  LMLVKLNSQA  RLSSMVKKVR  LPSRCE..PP
T12   VYHSKYKPKR  ......LGND  IALMKLAGPL  TFNEMIQPVC  LPNSEENFPD
```

Fig. 2A

|       | 351        |           |            |              | 400      |
|-------|------------|-----------|------------|--------------|----------|
| Prom  | TTSCHILGWG | KTAD..GDFP | DTIQCAYIHL | VSREECEHA.  | .YPGQITQNM |
| Try1  | GTKCLISGWG | NTASSGADYP | DELQCLDAPV | LSQAKCEAS.  | .YPGKITSNM |
| Scce  | GTTCTVSGWG | TTTSPDVTFP | SDLMCVDVKL | ISPQDCTKV.  | .YKDLLENSM |
| Heps  | GKICTVTGWG | NT.QYYGQQA | GVLQEARVPI | ISNDVCNGAD  | FYGNQIKPKM |
| T12   | GKVCWTSGWG | AT.EDGGDAS | PVLNHAAVPL | ISNKDLQPQG  | RVRWHHLPLH |

|       | 401        |           | 421 |
|-------|------------|-----------|-----|
| Prom  | LCAGDEKYGK | .DSCQGDSGG | P   |
| Try1  | FCVGFLEGGK | .DSCQGDSGG | P   |
| Scce  | LCAGIPDSKK | .NACNGDSGG | P   |
| Heps  | FCAGYPEG.G | IDACQGDSGG | P   |
| T12   | ALRGLPDGWR | WNSCQGDSGG | P   |

Fig. 2B

```
   1 CGGGAAAGGG CTGTGTTTAT GGGAAGCCAG TAACACTGTG GCCTACTATC
  51 TCTTCCGTGG TGCCATCTAC ATTTTTGGGA CTCGGGAATT ATGAGGTAGA
                                                          1
 101 GGTGGAGGCG GAGCCGGATG TCAGAGGTCC TGAAATAGTC ACCATGGGGG
 151 AAAATGATCC GCCTGCTGTT GAAGCCCCCT TCTCATTCCG ATCGCTTTTT
 201 GGCCTTGATG ATTTGAAAAT AAGTCCTGTT GCACCAGATG CAGATGCTGT
 251 TGCTGCACAG ATCCTGTCAC TGCTGCCATT TGAAGTTTTT TCCCAATCAT
 301 CGTCATTGGG GATCATTGCA TTGATATTAG CACTGGCCAT TGGTCTGGGC
 351 ATCCACTTCG ACTGCTCAGG GAAGTACAGA TGTCGCTCAT CCTTTAAGTG
 401 TATCGAGCTG ATAACTCGAT GTGACGGAGT CTCGGATTGC AAAGACGGGG
 451 AGGACGAGTA CCGCTGTGTC CGGGTGGGTG GTCAGAATGC CGTGCTCCAG
 501 GTGTTCACAG CTGCTTCGTG GAAGACCATG TGCTCCGATG ACTGGAAGGG
 551 TCACTACGCA AATGTTGCCT GTGCCCAACT GGGTTTCCCA AGCTATGTGA
 601 GTTCAGATAA CCTCAGAGTG AGCTCGCTGG AGGGGCAGTT CCGGGAGGAG
 651 TTTGTGTCCA TCGATCACCT CTTGCCAGAT GACAAGGTGA CTGCATTACA
 701 CCACTCAGTA TATGTGAGGG AGGGATGTGC CTCTGGCCAC GTGGTTACCT
 751 TGCAGTGCAC AGCCTGTGGT CATAGAAGGG CTACAGCTC ACGCATCGTG
 801 GGTGGAAACA TGTCCTTGCT CTCGCAGTGG CCCTGGCAGG CCAGCCTTCA
 851 GTTCCAGGGC TACCACCTGT GCGGGGGCTC TGTCATCACG CCCCTGTGGA
 901 TCATCACTGC TGCACACTGT GTTTATGACT TGTACCTCCC CAAGTCATGG
 951 ACCATCCAGG TGGGTCTAGT TTCCCTGTTG GACAATCCAG CCCCATCCCA
1001 CTTGGTGGAG AAGATTGTTT ACCACAGCAA GTACAAGCCA AAGAGGCTGG
1051 GCAATGACAT CGCCCTTATG AAGCTGGCCG GCCACTCAC GTTCAATGAA
1101 ATGATCCAGC CTGTGTGCCT GCCCAACTCT GAAGAGAACT TCCCCGATGG
1151 AAAAGTGTGC TGGACGTCAG GATGGGGGGC CACAGAGGAT GGAGGTGACG
1201 CCTCCCCTGT CCTGAACCAC GCGGCCGTCC CTTTGATTTC AACAAAGAT
1251 CTGCAACCAC AGGGACGTGT ACGGTGGCAT CATCTCCCCC TCCATGCTCT
1301 GCGCGGGCTA CCTGACGGGT GGCGTTGGAA CAGCTGCCAG GGGACAGCG
1351 GGGGGCCCCT GGTGTGTCAA GAGAGGAGGC TGTGGAAGTT AGTGGGAGCG
1401 ACCAGCTTTG GCATCGGCTG CGCAGACGTG AACAAGCCTG GGTGTACAC
1451 CCGTGTCACC TCCTTCCTGG ACTGGATCCA CGAGCAGATG GAGAGAGACC
               2
1501 TAAAAACCTG AAGAGGAAGG GGACAAGTAG CCACCTGAGT TCCTGAGGTG
1551 ATGAAGACAG CCCGATCCTC CCCTGGACTC CCGTGTAGGA ACCTGCACAC
1601 GAGCAGACAC CCTTGGAGCT CTGAGTTCCG GCACCAGTAG CGGGCCCGAA
```

Fig. 3A

```
1651 AGAGGCACCC TTCCATCTGA TTCCAGCACA ACCTTCAAGC TGCTTTTTGT
1701 TTTTTGTTTT TTTGAGGTGG AGTCTCGCTC TGTTGCCCAG GCTGGAGTGC
1751 AGTGGCGAAA TACCCTGCTC ACTGCAGCCT CCGCTTCCCT GGTTCAAGCG
1801 ATTCTCTTGC CTCAGCTTCC CCAGTAGCTG GGACCACAGG TGCCCGCCAC
1851 CACACCCAAC TAATTTTTGT ATTTTTAGTA GAGACAGGGT TTCACCATGT
1901 TGGCCAGGCT GCTCTCAAAC CCCTGACCTC AAATGATGTG CCTGCTTCAG
1951 CCTCCCACAG TGCTGGGATT ACAGGCATGG GCCACCACGC CTAGCCTCAC
2001 GCTCCTTTCT GATCTTCACT AAGAACAAAA GAAGCAGCAA CTTGCAAGGG
2051 CGGCCTTTCC CACTGGTCCA TCTGGTTTTC TCTCCAGGGT CTTGCAAAAT
2101 TCCTGACGAG ATAAGCAGTT ATGTGACCTC ACGTGCAAAG CCACCAACAG
2151 CCACTCAGAA AAGACGCACC AGCCCAGAAG TGCAGAACTG CAGTCACTGC
2201 ACGTTTTCAT CTTTAGGGAC CAGAACCAAA CCCACCCTTT CTACTTCCAA
2251 GACTTATTTT CACATGTGGG GAGGTTAATC TAGGAATGAC TCGTTTAAGG
2301 CCTATTTTCA TGATTTCTTt gtagcatttg gtgcttgacg tattattgtc
                                                        3
2351 ctttgattcc aaataatatg tttccttccc tcaaaaaaaa aaaaaaaaa
2401 aaaaaaaaaa aaaaaa*
```

1 = Kozak's consensus sequence for initiation of translation
2 = Stop codon
3 = Polyadenylation signal
The underlined sequence represents the open reading frame.
*Lowercase sequence was obtained from the EST database.

Fig. 3B

```
  1 MGENDPPAVE APFSFRSLFG LDDLKISPVA PDADAVAAQI LSLLPFEVFS
                1
 51 QSSSLGIIAL ILALAIGLGI HFDCSGKYRC RSSFKCIELI TRCDGVSDCK

101 DGEDEYRCVR VGGQNAVLQV FTAASWKTMC SDDWKGHYAN VACAQLGFPS
                                        2
151 YVSSDNLRVS SLEGQFREEF VSIDHLLPDD KVTALHHSVY VREGCASGHV

201 VTLQCTACGH RRGYSSRIVG GNMSLLSQWP WQASLQFQGY HLCGGSVITP
                                  3
251 LWIITAAHCV YDLYLPKSWT IQVGLVSLLD NPAPSHLVEK IVYHSKYKPK

301 RLGNDIALMK LAGPLTFNEM IQPVCLPNSE ENFPDGKVCW TSGWGATEDG

351 GDASPVLNHA AVPLISNKDL QPQGRVRWHH LPLHALRGLP DGWRWNSCQG

401 DSGGPLVCQE RRLWKLVGAT SFGIGCADVN KPGVYTRVTS FLDWIHEQME

451 RDLKT
```

1 = Potential transmembrane domain
2 = Potential cleavage/activation site
3 = Catalytic domain

Fig. 4

TADG12

```
1   TGGGTGGTGACGGGCGGCACTGTGTTTATGACTTGTACCTCCCCAAGTCATGACCATC
    W  V  V  T  A  A  H  C  V  Y  D  L  Y  L  P  K  S  W  T  I
61  CAGGTGGGGTCTAGTTTCCCTGTTGGACAATCCAGCCCCCATCCCCACTTGGTGGAGAAGATT
    Q  V  G  L  V  S  L  L  D  N  P  A  P  S  H  L  V  E  K  I
121 GTCTACCACAGCAAGTACAAGAGGCTGGGCAACGACATCGCCCTCCTA
    V  Y  H  S  K  Y  K  P  K  R  L  G  N  D  I  A  L  L
```

Fig. 6A

TADG12-V

```
1   GGGTGGTGACGGGCGGCACTGTGTTTATGAGATTGTAGCTCCCTAGAGAAAGGGCAGACA
    V  V  T  A  A  H  C  V  Y  E  I  V  A  P  R  E  R  A  D  R
61  GAAGAGGAAGGAAGCTCCTGTGCTGGAGGAAACCCACAAAAATGAAAGGACCTAGACCTT
    R  G  R  K  L  L  C  W  R  K  P  T  K  M  K  G  P  R  P  S
121 CCCATAGCTAATTCCAGTGGACCATGTTATGGCAGATACAGGCTTGTACCTCCCCAAGTC
    H  S  *
181 ATGGACCATCCAGTGGGTCTAGTTTCCCTGTTGGACAATCCAGCCCCATCCCCACTTGGT
241 GGAGAAGATTGTCTACCACAGCAAGTACAAGCCAAAGAGGCTGGGCAACGACATCGCCCT
301 CCTAATCACTAGTGCGGGCCGCCTGCAGG
```

Fig. 6B

⇒ indicates the position of the TADG12 variant insert.
The underlined portion represents the insert.

US 6,291,663 B1

TADG-12: A NOVEL TRANSMEMBRANE SERINE PROTEASE OVEREXPRESSED IN A OVARIAN CARCINOMA

BACKGROUND OF THE INVENTION

1. Field of the Invention

The present invention relates generally to the fields of cellular biology and the diagnosis of neoplastic disease. More specifically, the present invention relates to a transmembrane serine protease termed Tumor Antigen Derived Gene-12 (TADG-12), which is overexpressed in ovarian carcinoma.

2. Description of the Related Art

Proteases have been associated directly with tumor growth, shedding of tumor cells and invasion of target organs. Individual classes of proteases are involved in, but not limited to (1) the digestion of stroma surrounding the initial tumor area, (2) the digestion of the cellular adhesion molecules to allow dissociation of tumor cells; and (3) the invasion of the basement membrane for metastatic growth and the activation of both tumor growth factors and angiogenic factors.

The prior art is deficient in the lack of the complete identification of the proteases overexpressed in carcinoma. Specifically, TADG-12, a novel transmembrane serine protease, has not been previously identified in either nucleic acid or protein form. The present invention fulfills this longstanding need and desire in the art.

SUMMARY OF THE INVENTION

The present invention discloses TADG-12, a new member of the Tumor Antigen Derived Gene (TADG) family. TADG-12 is a novel transmembrane serine protease overexpressed in ovarian carcinoma.

In one embodiment of the present invention, there is provided a DNA encoding a TADG-12 protein selected from the group consisting of: (a) isolated DNA which encodes a TADG-12 protein; (b) isolated DNA which hybridizes to isolated DNA of (a) above and which encodes a TADG-12 protein; and (c) isolated DNA differing from the isolated DNAs of (a) and (b) above in codon sequence due to the degeneracy of the genetic code, and which encodes a TADG-12 protein.

In another embodiment of the present invention, there is provided a vector capable of expressing the DNA of the present invention adapted for expression in a recombinant cell and regulatory elements necessary for expression of the DNA in the cell.

In yet another embodiment of the present invention, there is provided a host cell transfected with the vector of the present invention, the vector expressing a TADG-12 protein.

In still yet another embodiment of the present invention, there is provided a method of detecting expression of a TADG-12 mRNA, comprising the steps of: (a) contacting mRNA obtained from the cell with the labeled hybridization probe; and (b) detecting hybridization of the probe with the mRNA.

The TADG-12 gene product has several potential application 1) as a target; 2) for antisense inhibition of its expression; 3) for gene therapy; 4) for vaccination; and 5) for inhibition by small molecular protease protein inhibitors.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIGS. 2A and 2B show the amino sequence of the catalytic domain of TADG-12 compared to known serine proteases including protease M, trypsinogen 1, stratum corneum chymotryptic enzyme, and hepsin.

FIGS. 3A and 3B show the known nucleotide sequence of TADG-12 transcript as identified by PCR and cloning. It includes a Kozak initiation sequence, an inframe stop codon and an overlapping sequence (100 bases) from the est data base which contains a poly A signal sequence and a poly A tail.

FIG. 4 shows the amino sequence of the TADG-12 open reading frame, including a putative cytoplasmic domain, a transmembrane domain, a protease cleavage/activation site and a carboxy terminal protease domain.

FIG. 6A shows the amino acid/nucleotide sequence of the 5' end of the catalytic domain (His—Asp) of TADG-12. FIG. 6B shows amino acid/nucleotide sequence of the TADG-12-variant transcript indicating the inserted sequence as underlined and showing a truncated peptide due to the presence of a stop codon in this variant.

DETAILED DESCRIPTION OF THE INVENTION

Figure 1:
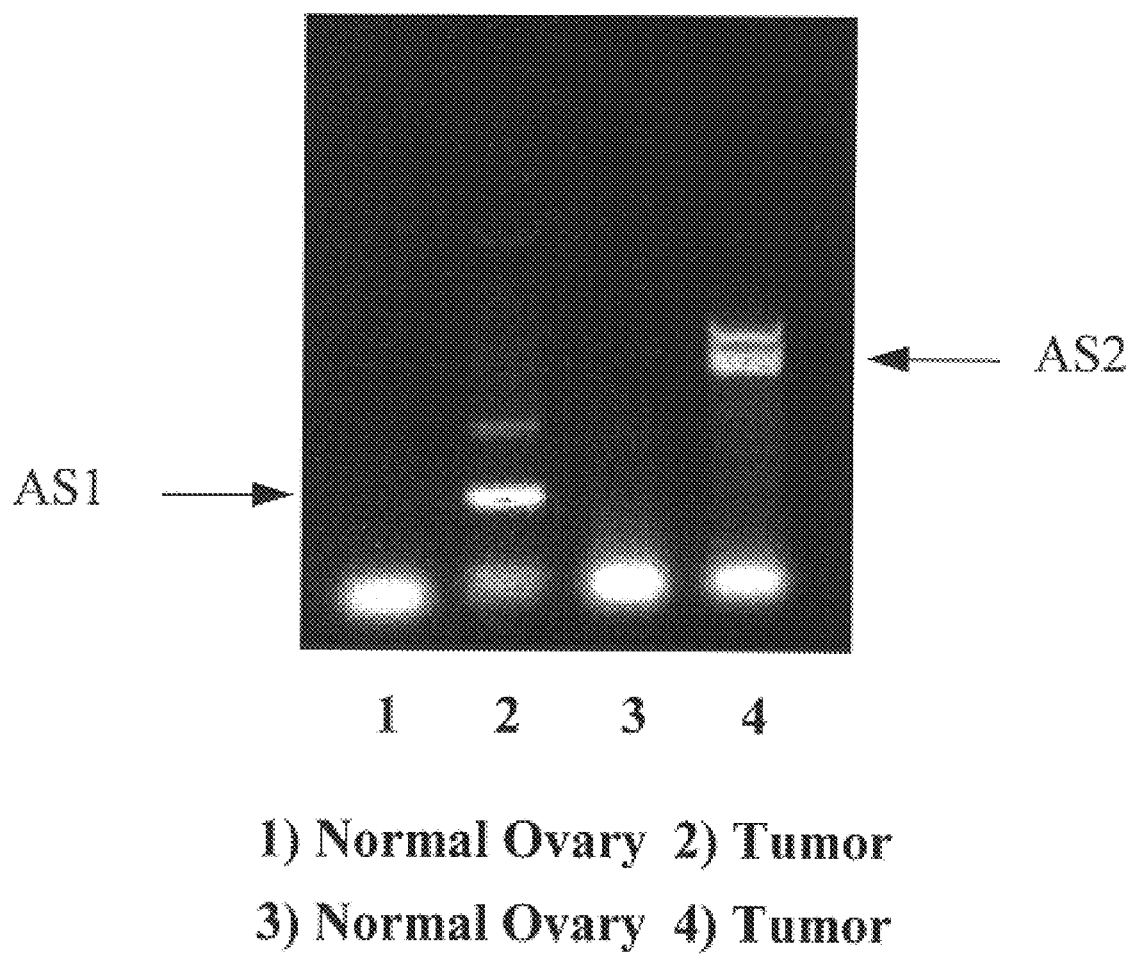
FIG. 1 shows PCR amplification of cDNA derived from normal ovary (lanes 1 & 3) or ovarian carcinoma (lanes 2 & 4) using redundant primers to the conserved histidine domain (sense) and conserved aspartic acid domain (antisense), lanes 1 & 2. The conserved histidine domain (sense) and the conserved serine domain (antisense) lanes 3 & 4. The anticipated size of the PCR product for lanes 1 and 2 is approximately 200 bp and for lanes 3 & 4, approximately 500 bp. Note in lane 2, the expected product (lower band) is observed but in addition, a second PCR product (approximately 350 bp) is noted.

The TADG-12 cDNA is 2416 base pairs long (SEQ ID No:1) and encoding for a 421 amino acid protein (SEQ ID No:2). A variant form, TADG12-v (SEQ ID No:3), encodes a 42 amino acid protein (SEQ ID No:4). The availability of the TADG-12 gene opens the way for a number studies that can lead to various applications. For example, the TADG-12 gene can be used as a diagnostic or therapeutic target in ovarian carcinoma and other carcinomas including breast, prostate, lung and colon.

In accordance with the present invention there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual (1982); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins eds. (1985)]; "Transcription and Translation" [B. D. Hames & S. J. Higgins eds. (1984)]; "Animal Cell Culture" [R. I. Freshney, ed. (1986)];

"Immobilized Cells And Enzymes" [IRL Press, (1986)]; B. Perbal, "A Practical Guide To Molecular Cloning" (1984).

Therefore, if appearing herein, the following terms shall have the definitions set out below.

As used herein, the term "cDNA" shall refer to the DNA copy of the mRNA transcript of a gene.

As used herein, the term "derived amino acid sequence" shall mean the amino acid sequence determined by reading the triplet sequence of nucleotide bases in the cDNA.

As used herein the term "screening a library" shall refer to the process of using a labeled probe to check whether, under the appropriate conditions, there is a sequence complementary to the probe present in a particular DNA library. In addition, "screening a library" could be performed by PCR.

As used herein, the term "PCR" refers to the polymerase chain reaction that is the subject of U.S. Pat. Nos. 4,683,195 and 4,683,202 to Mullis, as well as other improvements now known in the art.

The amino acid described herein are preferred to be in the "L" isomeric form. However, residues in the "D" isomeric form can be substituted for any L-amino acid residue, as long as the desired functional property of immunoglobulin-binding is retained by the polypeptide. $NH_2$ refers to the free amino group present at the amino terminus of a polypeptide. COOH refers to the free carboxy group present at the carboxy terminus of a polypeptide. In keeping with standard polypeptide nomenclature, *J Biol. Chem.*, 243:3552–59 (1969), abbreviations for amino acid residues are known in the art.

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues.

A "replicon" is any genetic element (e.g., plasmid, chromosome, virus) that functions as an autonomous unit of DNA replication in vivo; i.e., capable of replication under its own control.

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure herein according to the normal convention of giving only the sequence in the 5' to 3' direction along the nontranscribed strand of DNA (i.e., the strand having a sequence homologous to the mRNA).

An "origin of replication" refers to those DNA sequences that participate in DNA synthesis.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site, as well as protein binding domains (consensus sequences) responsible for the binding of RNA polymerase. Eukaryotic promoters often, but not always, contain "TATA" boxes and "CAT" boxes. Prokaryotic promoters contain Shine-Dalgarno sequences in addition to the −10 and −35 consensus sequences.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

A "signal sequence" can be included near the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

The term "oligonucleotide", as used herein in referring to the probe of the present invention, is defined as a molecule comprised of two or more ribonucleotides, preferably more than three. Its exact size will depend upon many factors which, in turn, depend upon the ultimate function and use of the oligonucleotide.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use the method. For example, for diagnostic applications, depending on the complexity of the target sequence, the oligonucleotide primer typically contains 15–25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementary with the sequence or hybridize therewith and thereby form the template for the synthesis of the extension product.

As used herein, the terms "restriction endonucleases" and "irestriction enzymes" refer to enzymes, each of which cut double-stranded DNA at or near a specific nucleotide sequence.

A cell has been "transformed" by exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or ancestor by mitosis. A "cell line" is a clone of a primary cell that is capable of stable growth in vitro for many generations.

Two DNA sequences are "substantially homologous" when at least about 75% (preferably at least about 80%, and most preferably at least about 90% or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

A "heterologous' region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. In another example, coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

The labels most commonly employed for these studies are radioactive elements, enzymes, chemicals which fluoresce when exposed to ultraviolet light, and others. A number of fluorescent materials are known and can be utilized as labels. These include, for example, fluorescein, rhodamine, auramine, Texas Red, AMCA blue and Lucifer Yellow. A particular detecting material is anti-rabbit antibody prepared in goats and conjugated with fluorescein through an isothiocyanate.

Proteins can also be labeled with a radioactive element or with an enzyme. The radioactive label can be detected by any of the currently available counting procedures. The preferred isotope may be selected from $^{3}H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$.

Enzyme labels are likewise useful, and can be detected by any of the presently utilized calorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, β-glucuronidase, β-D-glucosidase, β-D-galactosidase, urease, glucose oxidase plus peroxidase and alkaline phosphatase. U.S. Pat. Nos. 3,654,090, 3,850,752, and 4,016,043 are referred to by way of example for their disclosure of alternate labeling material and methods.

A particular assay system developed and utilized in the art is known as a receptor assay. In a receptor assay, the material to be assayed is appropriately labeled and then certain cellular test colonies are inoculated with a quantitiy of both the label after which binding studies are conducted to determine the extent to which the labeled material binds to the cell receptors. In this way, differences in affinity between materials can be ascertained.

An assay useful in the art is known as a "cis/trans" assay. Briefly, this assay employs two genetic constructs, one of which is typically a plasmid that continually expresses a particular receptor of interest when transfected into an appropriate cell line, and the second of which is a plasmid that expresses a reporter such as luciferase, under the control of a receptor/ligand complex. Thus, for example, if it is desired to evaluate a compound as a ligand for a particular receptor, one of the plasmids would be a construct that results in expression of the receptor in the chosen cell line, while the second plasmid would possess a promoter linked to the luciferase gene in which the response element to the particular receptor is inserted. If the compound under test is an agonist for the receptor, the ligand will complex with the receptor, and the resulting complex will bind the response element and initiate transcription of the luciferase gene. The resulting chemiluminescence is then measured photometrically, and dose response curves are obtained and compared to those of known ligands. The foregoing protocol is described in detail in U.S. Pat. No. 4,981,784.

As used herein, the term "host" is meant to include not only prokaryotes but also eukaryotes such as yeast, plant and animal cells. A recombinant DNA molecule or gene which encodes a human TADG-12 protein of the present invention can be used to transform a host using any of the techniques commonly known to those of ordinary skill in the art. Especially preferred is the use of a vector containing coding sequences for the gene which encodes a human TADG-12 protein of the present invention for purposes of prokaryote transformation. Prokaryotic hosts may include *E. coli, S. tymphimurium, Serratia marcescens* and *Bacillus subtilis*. Eukaryotic hosts include yeasts such as *Pichia pastoris*, mammalian cells and insect cells.

In general, expression vectors containing promoter sequences which facilitate the efficient transcription of the inserted DNA fragment are used in connection with the host. The expression vector typically contains an origin of replication, promoter(s), terminator(s), as well as specific genes which are capable of providing phenotypic selection in transformed cells. The transformed hosts can be fermented and cultured according to means known in the art to achieve optimal cell growth.

The invention includes a substantially pure DNA encoding a TADG-12 protein, a strand of which DNA will hybridize at high stringency to a probe containing a sequence of at least 15 consecutive nucleotides of the sequence in FIGS. 3A and 3B (SEQ ID NO:1). The protein encoded by the DNA of this invention may share at least 80% sequence identity (preferably 85%, more preferably 90%, and most preferably 95%) with the amino acids listed in FIG. 4 (SEQ ID NO:2). More preferably, the DNA includes the coding sequence of the nucleotides of FIGS. 3A and 3B (SEQ ID NO:1), or a degenerate variant of such a sequence.

The probe to which the DNA of the invention hybridizes preferably consists of a sequence of at least 20 consecutive nucleotides, more preferably 40 nucleotides, even more preferably 50 nucleotides, and most preferably 100 nucleotides or more (up to 100%) of the coding sequence of the nucleotides listed in FIGS. 3A and 3B (SEQ ID NO:1) or the complement thereof. Such a probe is useful for detecting expression of TADG-12 in a human cell by a method including the steps of (a) contacting mRNA obtained from the cell with the labeled hybridization probe; and (b) detecting hybridization of the probe with the mRNA.

This invention also includes a substantially pure DNA containing a sequence of at least 15 consecutive nucleotides (preferably 20, more preferably 30, even more preferably 50, and most preferably all) of the region from nucleotides 1 to 2416 of the nucleotides listed in FIGS. 3A and 3B (SEQ ID NO:1). The present invention also comprises antisense oligonucleotides directed against this novel DNA. Given the teachings of the present invention, a person having ordinary skill in this art would readily be able to develop antisense oligonucleotides directed against this DNA.

By "high stringency" is meant DNA hybridization and wash conditions characterized by high temperature and low salt concentration, e.g., wash conditions of 65° C. at a salt concentration of approximately 0.1×SSC, or the functional equivalent thereof. For example, high stringency conditions may include hybridization at about 42° C. in the presence of about 50% formamide; a first wash at about 65° C. with about 2×SSC containing 1% SDS; followed by a second wash at about 65° C. with about 0.1×SSC.

By "substantially pure DNA" is meant DNA that is not part of a milieu in which the DNA naturally occurs, by virtue of separation (partial or total purification) of some or all of the molecules of that milieu, or by virtue of alteration of sequences that flank the claimed DNA. The term therefore includes, for example, a recombinant DNA which is incorporated into a vector, into an autonomously replicating plasmid or virus, or into the genomic DNA of a prokaryote or eukaryote; or which exists as a separate molecule (e.g., a cDNA or a genomic or cDNA fragment produced by polymerase chain reaction (PCR) or restriction endonuclease digestion) independent of other sequences. It also includes a recombinant DNA which is part of a hybrid gene encoding additional polypeptide sequence, e.g., a fusion protein. Also included is a recombinant DNA which includes a portion of the nucleotides listed in FIG. 6 (SEQ ID NO:3) which encodes an alternative splice variant of TADG-12.

The DNA may have at least about 70% sequence identity to the coding sequence of the nucleotides listed in FIGS. 3A and 3B (SEQ ID NO:1), preferably at least 75% (e.g. at least 80%); and most preferably at least 90%. The identity between two sequences is a direct function of the number of matching or identical positions. When a subunit position in both of the two sequences is occupied by the same monomeric subunit, e.g., if a given position is occupied by an adenine in each of two DNA molecules, then they are identical at that position. For example, if 7 positions in a sequence 10 nucleotides in length are identical to the corresponding positions in a second 10-nucleotide sequence, then the two sequences have 70% sequence identity. The length of comparison sequences will generally be at least 50 nucleotides, preferably at least 60 nucleotides, more preferably at least 75 nucleotides, and most preferably 100 nucleotides. Sequence identity is typically measured using sequence analysis software (e.g., Sequence Analysis Software Package of the Genetics Computer Group, University of Wisconsin Biotechnology Center, 1710 University Avenue, Madison, Wis. 53705).

The present invention comprises a vector comprising a DNA sequence which encodes a human TADG-12 protein and the vector is capable of replication in a host which comprises, in operable linkage: a) an origin of replication; b) a promoter; and c) a DNA sequence coding for said protein. Preferably, the vector of the present invention contains a portion of the DNA sequence shown in SEQ ID No:1. A "vector" may be defined as a replicable nucleic acid construct, e.g., a plasmid or viral nucleic acid. Vectors may be used to amplify and/or express nucleic acid encoding TADG-12 protein. An expression vector is a replicable construct in which a nucleic acid sequence encoding a polypeptide is operably linked to suitable control sequences capable of effecting expression of the polypeptide in a cell. The need for such control sequences will vary depending upon the cell selected and the transformation method chosen. Generally, control sequences include a transcriptional promoter and/or enhancer, suitable mRNA ribosomal binding sites, and sequences which control the termination of transcription and translation. Methods which are well known to those skilled in the art can be used to construct expression vectors containing appropriate transcriptional and translational control signals. See for example, the techniques described in Sambrook et al., 1989, *Molecular Cloning: A Laboratory Manual* (2nd Ed.), Cold Spring Harbor Press, New York. A gene and its transcription control sequences are defined as being "operably linked" if the transcription control sequences effectively control the transcription of the gene. Vectors of the invention include, but are not limited to, plasmid vectors and viral vectors. Preferred viral vectors of the invention are those derived from retroviruses, adenovirus, adeno-associated virus, SV40 virus, or herpes viruses.

By a "substantially pure protein" is meant a protein which has been separated from at least some of those components which naturally accompany it. Typically, the protein is substantially pure when it is at least 60%, by weight, free from the proteins and other naturally-occurring organic molecules with which it is naturally associated in vivo. Preferably, the purity of the preparation is at least 75%, more preferably at least 90%, and most preferably at least 99%, by weight. A substantially pure TADG-12 protein may be obtained, for example, by extraction from a natural source; by expression of a recombinant nucleic acid encoding an TADG-12 polypeptide; or by chemically synthesizing the protein. Purity can be measured by any appropriate method, e.g., column chromatography such as immunoaffinity chromatography using an antibody specific for TADG-12, polyacrylamide gel electrophoresis, or HPLC analysis. A protein is substantially free of naturally associated components when it is separated from at least some of those contaminants which accompany it in its natural state. Thus, a protein which is chemically synthesized or produced in a cellular system different from the cell from which it naturally originates will be, by definition, substantially free from its naturally associated components. Accordingly, substantially pure proteins include eukaryotic proteins synthesized in $E.\ coli$, other prokaryotes, or any other organism in which they do not naturally occur.

In addition to substantially full-length proteins, the invention also includes fragments (e.g., antigenic fragments) of the TADG-12 protein (SEQ ID No:2). As used herein, "fragment," as applied to a polypeptide, will ordinarily be at least 10 residues, more typically at least 20 residues, and preferably at least 30 (e.g., 50) residues in length, but less than the entire, intact sequence. Fragments of the TADG-12 protein can be generated by methods known to those skilled in the art, e.g., by enzymatic digestion of naturally occurring or recombinant TADG-12 protein, by recombinant DNA techniques using an expression vector that encodes a defined fragment of TADG-12, or by chemical synthesis. The ability of a candidate fragment to exhibit a characteristic of TADG-12 (e.g., binding to an antibody specific for TADG-12) can be assessed by methods described herein. Purified TADG-12 or antigenic fragments of TADG-12 can be used to generate new antibodies or to test existing antibodies (e.g., as positive controls in a diagnostic assay) by employing standard protocols known to those skilled in the art. Included in this invention are polyclonal antisera generated by using TADG-12 or a fragment of TADG-12 as the immunogen in, e.g., rabbits. Standard protocols for monoclonal and polyclonal antibody production known to those skilled in this art are employed. The monoclonal antibodies generated by this procedure can be screened for the ability to identify recombinant TADG-12 cDNA clones, and to distinguish them from known cDNA clones.

Further included in this invention are TADG-12 proteins which are encoded at least in part by portions of SEQ ID NO:2, e.g., products of alternative mRNA splicing or alternative protein processing events, or in which a section of TADG-12 sequence has been deleted. The fragment, or the intact TADG-12 polypeptide, may be covalently linked to another polypeptide, e.g. which acts as a label, a ligand or a means to increase antigenicity.

The invention also includes a polyclonal or monoclonal antibody which specifically binds to TADG-12. The invention encompasses not only an intact monoclonal antibody, but also an immunologically-active antibody fragment, e.g., a Fab or $(Fab)_2$ fragment; an engineered single chain Fv molecule; or a chimeric molecule, e.g., an antibody which contains the binding specificity of one antibody, e.g., of murine origin, and the remaining portions of another antibody, e.g., of human origin.

In one embodiment, the antibody, or a fragment thereof, may be linked to a toxin or to a detectable label, e.g. a radioactive label, non-radioactive isotopic label, fluorescent label, chemiluminescent label, paramagnetic label, enzyme label, or colorimetric label. Examples of suitable toxins include diphtheria toxin, Pseudomonas exotoxin A, ricin, and cholera toxin. Examples of suitable enzyme labels include malate hydrogenase, staphylococcal nuclease, delta-5-steroid isomerase, alcohol dehydrogenase, alpha-glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, glucoamylase, acetylcholinesterase, etc. Examples of suitable radioisotopic labels include $^3H$, $^{125}I$, $^{131}I$, $^{32}P$, $^{35}S$, $^{14}C$, etc.

Paramagnetic isotopes for purposes of in vivo diagnosis can also be used according to the methods of this invention. There are numerous examples of elements that are useful in magnetic resonance imaging. For discussions on in vivo nuclear magnetic resonance imaging, see, for example, Schaefer et al., (1989) $JACC$ 14, 472–480; Shreve et al., (1986) $Magn.\ Reson.\ Med.$ 3, 336–340; Wolf, G. L., (1984) $Physiol.\ Chem.\ Phys.\ Med.\ NMR$ 16, 93–95; Wesbey et al., (1984) $Physiol.\ Chem.\ Phys.\ Med.\ NMR$ 16, 145–155; Runge et al., (1984) $Invest.\ Radiol.$ 19, 408–415. Examples of suitable fluorescent labels include a fluorescein label, an isothiocyalate label, a rhodamine label, a phycoerythrin label, a phycocyanin label, an allophycocyanin label, an ophthaldehyde label, a fluorescamine label, etc. Examples of chemiluminescent labels include a luminal label, an isoluminal label, an aromatic acridinium ester label, an imidazole label, an acridinium salt label, an oxalate ester label, a luciferin label, a luciferase label, an aequorin label, etc.

Those of ordinary skill in the art will know of other suitable labels which may be employed in accordance with the present invention. The binding of these labels to antibodies or fragments thereof can be accomplished using standard techniques commonly known to those of ordinary skill in the art. Typical techniques are described by Kennedy et al., (1976) $Clin.\ Chim.\ Acta$ 70, 1–31; and Schurs et al., (1977) $Clin.\ Chim.\ Acta$ 81, 1–40. Coupling techniques mentioned in the latter are the glutaraldehyde method, the periodate method, the dimaleimide method, the m maleimidobenzyl-N-hydroxy-succinimide ester method. All of these methods are incorporated by reference herein.

Also within the invention is a method of detecting TADG-12 protein in a biological sample, which includes the steps of contacting the sample with the labeled antibody, e.g., radioactively tagged antibody specific for TADG-12, and determining whether the antibody binds to a component of the sample.

As described herein, the invention provides a number of diagnostic advantages and uses. For example, the TADG-12 protein is useful in diagnosing cancer in different tissues since this protein is highly overexpressed in tumor cells. Antibodies (or antigen-binding fragments thereof) which bind to an epitope specific for TADG-12, are useful in a method of detecting TADG-12 protein in a biological sample for diagnosis of cancerous or neoplastic transformation. This method includes the steps of obtaining a biological sample (e.g., cells, blood, plasma, tissue, etc.) from a patient suspected of having cancer, contacting the sample with a labeled antibody (e.g., radioactively tagged antibody) specific for TADG-12, and detecting the TADG-12 protein using standard immunoassay techniques such as an ELISA. Antibody binding to the biological sample indicates that the sample contains a component which specifically binds to an epitope within TADG-12.

Likewise, a standard Northern blot assay can be used to ascertain the relative amounts of TADG-12 mRNA in a cell or tissue obtained from a patient suspected of having cancer, in accordance with conventional Northern hybridization techniques known to those of ordinary skill in the art. This Northern assay uses a hybridization probe, e.g. radiolabelled TADG-12 cDNA, either containing the full-length, single stranded DNA having a sequence complementary to SEQ ID NO:1 (FIGS. 3A and 3B), or a fragment of that DNA sequence at least 20 (preferably at least 30, more preferably at least 50, and most preferably at least 100 consecutive nucleotides in length). The DNA hybridization probe can be labeled by any of the many different methods known to those skilled in this art.

Antibodies to the TADG-12 protein can be used in an immunoassay to detect increased levels of TADG-12 protein expression in tissues suspected of neoplastic transformation. These same uses can be achieved with Northern blot assays and analyses.

The present invention is directed to DNA encoding a TADG-12 protein selected from the group consisting of: (a) isolated DNA which encodes a TADG-12 protein; (b) isolated DNA which hybridizes to isolated DNA of (a) above and which encodes a TADG-12 protein; and (c) isolated DNA differing from the isolated DNAs of (a) and (b) above in codon sequence due to the degeneracy of the genetic code, and which encodes a TADG-12 protein. Preferably, the DNA has the sequence shown in SEQ ID No:1. More preferably, the DNA encodes a TADG-12 protein having the amino acid sequence shown in SEQ ID No:2.

The present invention is also directed to a vector capable of expressing the DNA of the present invention adapted for expression in a recombinant cell and regulatory elements necessary for expression of the DNA in the cell. Preferably, the vector contains DNA encoding a TADG-12 protein having the amino acid sequence shown in SEQ ID No:2.

The present invention is also directed to a host cell transfected with the vector described herein, said vector expressing a TADG-12 protein. Representative host cells include bacterial cells, yeast cells, mammalian cells and insect cells.

The present invention is also directed to an isolated and purified TADG-12 protein coded for by DNA selected from the group consisting of: (a) isolated DNA which encodes a TADG-12 protein; (b) isolated DNA which hybridizes to isolated DNA of (a) above and which encodes a TADG-12 protein; and (c) isolated DNA differing from the isolated DNAs of (a) and (b) above in codon sequence due to the degeneracy of the genetic code, and which encodes a TADG-12 protein. Preferably, the isolated and purified TADG-12 protein of claim 9 having the amino acid sequence shown in SEQ ID No:2.

The present invention is also directed to a method of detecting expression of the protein described herein, comprising the steps of: (a) contacting mRNA obtained from the cell with the labeled hybridization probe; and (b) detecting hybridization of the probe with the mRNA.

A number of potential applications are possible for the TADG-12 gene and gene product. It may be useful as a therapeutic target in anti-sense inhibition of its expression or inhibition of its activity by small molecular protease protein inhibitors. It may also be useful as a vaccine target. Finally, it is possible that gene therapy applications utilizing TADG-12 may prove to be promising.

The following examples are given for the purpose of illustrating various embodiments of the invention and are not meant to limit the present invention in any fashion.

EXAMPLE 1
Tissue Collection and Storage

Upon patient hysterectomy, bilateral salpingo-oophorectomy, or surgical removal of neoplastic tissue, the specimen is retrieved and placed on ice. The specimen was then taken to the resident pathologist for isolation and identification of specific tissue samples. Finally, the sample was frozen in liquid nitrogen, logged into the laboratory record and stored at $-80°$ C. Additional specimens were frequently obtained from the Cooperative Human Tissue Network (CHTN). These samples were prepared by the CHTN and shipped on dry ice. Upon arrival, these specimens were logged into the laboratory record and stored at $-80°$ C.

EXAMPLE 2
mRNA Isolation and CDNA Synthesis

Forty-one ovarian tumors (10 low malignant potential tumors and 31 carcinomas) and 10 normal ovaries were obtained from surgical specimens and frozen in liquid nitrogen. The human ovarian carcinoma cell lines SW 626 and Caov 3, the human breast carcinoma cell lines MDA-MB-231 and MDA-MB-435S, and the human uterine cervical carcinoma cell line Hela were purchased from the American Type Culture Collection (Rockville, Md.). Cells were cultured to subconfluency in Dulbecco's modified Eagle's medium, suspended with 10% (v/v) fetal bovine serum and antibiotics.

Messenger RNA (mRNA) isolation was performed according to the manufacturer's instructions using the Mini RiboSep™ Ultra mRNA isolation kit purchased from Becton Dickinson (cat. #30034). This was an oligo(dt) chromatography based system of mRNA isolation. The amount of mRNA recovered was quantitated by UV spectrophotometry.

First strand complementary DNA (cDNA) was synthesized using 5.0 mg of mRNA and either random hexamer or oligo(dT) primers according to the manufacturer's protocol utilizing a first strand synthesis kit obtained from Clontech (cat.# K1402-1). The purity of the CDNA was evaluated by PCR using primers specific for the p53 gene. These primers span an intron such that pure cDNA can be distinguished from cDNA that is contaminated with genomic DNA.

EXAMPLE 3
Differential PCR Display Identification of TADG-12

TADG-12 was identified by differential PCR display using normal ovarian tissue and ovarian carcinoma samples. TADG-12 was discovered utilizing redundant primers to the conserved sequences of the catalytic triad (His-Asp-Ser) essential for serine protease activity. TADG-12 was identified with the primers specific for the conserved histidine, sense 5'-TGGGTIGTIACIGCIGCICA-3' (SEQ ID No: 9), and the conserved aspartic acid, antisense 5'-ARIARIGCIATITCITTICC-3' (SEQ ID No: 10).

Reactions were carried out as follows: first strand cDNA generated from 50 ng of mRNA were used as template in the presence of 1.0 mM $MgCl_2$, 0.2 mM dNTPs, 0.025 U Taq polymerase/ml of reaction, and 1xbuffer supplied with enzyme. In addition, primers must be added to the PCR reaction. Degenerate primers which may amplify a variety of cDNAs were used at a final concentration of 2.0 mM each, whereas primers which amplify specific cDNAs were added to a final concentration of 0.2 mM each.

After initial denaturation at $95°$ C. for 3 minutes, thirty cycles of PCR were carried out in a Perkin Elmer Gene Amp 2400 thermal cycler. Each cycle consists of 30 seconds of denaturation at $95°$ C., 30 seconds of primer annealing at the appropriate annealing temperature, and 30 seconds of extension at 72° C. The final cycle was extended at 72° C. for 7 minutes. To ensure that the reaction succeeded, a fraction of the mixture was electrophoresed through a 2% agarose/TAE gel stained with ethidium bromide (final concentration 1 mg/ml). The annealing temperature varies according to the primers that are used in the PCR reaction. For the reactions involving degenerate primers, an annealing temperature of 48° C. was used. The appropriate annealing temperature for the TADG-12 specific primers is 60° C.

The results of the differential PCR amplification are shown in FIG. 1. The anticipated size of the PCR product for lanes 1 and 2 is approximately 200 bp and for lanes 3 & 4, approximately 500 bp. Note in lane 2, the expected product (lower band) is observed but in addition, a second PCR product (approximately 350 bp) is noted.

EXAMPLE 4
Subcloning of the Catalytic Domain of TADG-12

The PCR amplified catalytic domain of TADG-12 was subcloned into the Promega T-vector plasmid and the ligation products were used to transform JM109 competent cells according to the manufacturer's instructions (Promega cat. #A3610). Positive colonies were cultured for amplification, the plasmid DNA isolated by means of the Wizard™ Minipreps DNA purification system (Promega cat #A7500), and the plasmids were digested with ApaI and SacI restriction enzymes to determine the size of the insert. Plasmids with inserts of the size(s) visualized by the previously described PCR product gel electrophoresis were sequenced.

EXAMPLE 5
Sequencing of the Catalytic Domain of TADG-12

Utilizing a plasmid specific primer near the cloning site, sequencing reactions were carried out using PRISM™ Ready Reaction Dye Deoxy™ terminators (Applied Biosystems cat# 401384) according to the manufacturer's instructions. Residual dye terminators were removed from the completed sequencing reaction using a Centri-sep™ spin column (Princeton Separation cat.# CS-901). An Applied Biosystems Model 373A DNA Sequencing System was available and was used for sequence analysis.

In FIGS. 2A and 2B, the predicted amino acid sequence of the catalytic domain (amino acids 251–421 of SEQ ID No: 2) is compared to the amino acid sequences of other members of the serine protease family, including protease M (SEQ ID No:5), trypsinogen 1 (SEQ ID No:6), stratum corneum chymotryptic enzyme (SEQ ID No:7), and hepsin (SEQ ID No:8).

EXAMPLE 6
Isolation of a TADG-12 cDNA

Utilizing the catalytic domain described above as a probe to screen a cDNA ovarian carcinoma library, a cDNA was identified representing approximately 2300 b.p. of overlapping sequence with an open reading frame preceded by a Kozac consensus sequence (FIGS. 3A and 3B). A poly-A tail with homologous upstream sequence to TADG-12 was identified from the EST data base and is also included in FIGS. 3A and 3B. Translation of the open reading frame suggests a protease of 454 amino acids as shown in FIG. 4. It is noted that the TADG-12 protease encompasses the following domains: 1) a cytoplasmic domain; 2) a potential transmembrane domain; 3) a possible cleavage/activation site and 4) a catalytic domain.

EXAMPLE 7
Northern Blot Analysis of TADG-12 Expression

10 μg mRNAs were size separated by electrophoresis through a 1% formaldehyde-agarose gel in 0.02 M MOPS, 0.05 M sodium acetate (pH 7.0), and 0.001 M EDTA. The mRNAs were then blotted to Hybond-N (Amersham) by capillary action in 20×SSPE. The mRNAs are fixed to the membrane by baking for 2 hours at 80° C. The appropriate probes were radiolabelled utilizing the Prime-a-Gene Labeling System available from Promega (cat#U1100). The blots were probed and stripped according to the ExpressHyb Hybridization Solution protocol available from CLONTECH (cat.#8015-1 or 8015-2).

Figure 5:
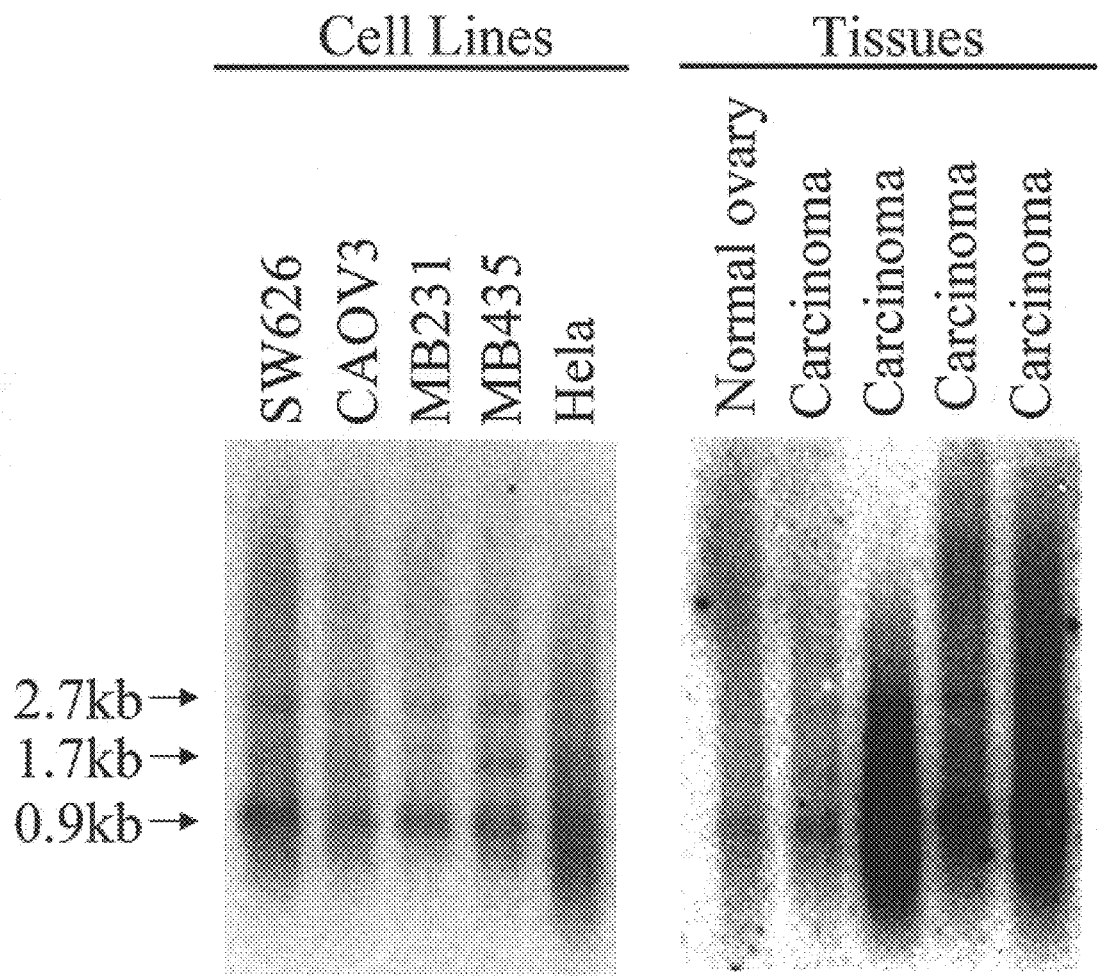
FIG. 5 shows northern blot analysis utilizing a cDNA probe to the unique 5' sequence of TADG-12, indicating a common transcript of 900 bp and two larger transcripts of 2.7 and 1.7 bp. Increased expression of TADG-12 transcript is noted in ovarian carcinoma and tumor cell lines.

Northern blot analysis utilizing a cDNA probe from the 5' domain of TADG-12 (Base #425–863) revealed three possible transcripts of 2.6 kb 1.7 kb and 0.9 kb (FIG. 5). The dominant transcript appears to the 0.9 kb size. The presence of transcripts are noted to be overexpressed in several subtypes of ovarian carcinomas. Probing Northern blots of adult tissues revealed low/no expression of the TADG-12 transcript (data not shown).

EXAMPLE 8
PCR Identification of an Alternative Transcript

During PCR amplification using the initial redundant primers (see FIG. 1), a second PCR product of greater bp size (approximately 290 bp) than anticipated was also identified as overexpressed when tumor cDNA was amplified. Subcloning and sequencing of this PCR product revealed that it contained approximately a 133 bp insert into the catalytic domain downstream from the primary histidine of the catalytic triad (FIG. 6). Such an insertion would result in a truncated protein product as an inframe stop codon is present downstream from the histidine as shown in FIG. 6. This altered version of the protease transcript (TADG-12-V) would abrogate TADG-12 proteolytic activity but may allow a truncated transmembrane protein to be synthesized. Again, it is noted that this transcript variant is found only in the carcinoma group and not in normal ovary.

EXAMPLE 9
Quantitative PCR Characterization of the Alternative Transcript

To access the expression of the TADG-12 variant compared to the expression of the standard protease the presence of both transcripts were examined in normal and ovarian carcinoma by PCR using a tubulin control. Specific oligonucleotide primers for TADG-12-V were synthesized which consisted of T-12-V Sense 5'-TCCAGGTGGGTCTAGTTTCC-3' (SEQ ID No: 11) and T-12-V Anti-sense 5'-CTCTTTGGCTTGTACTTGCT-3' (SEQ ID No: 12). The following oligonucleotide primers for the standard transcript of TADG-12 were synthesized as well: T12 Sense 5'-GAAACATGTCCTTGCTCTCG-3' (SEQ ID No: 13) and T12 Antisense 5'-ACTAACTTCCACAGCCTCCT-3' (SEQ ID No: 14). Quantitative-PCR was performed with a reaction mixture consisting of cDNA derived from 50 ng of mRNA, 5 pmol each of primers for the appropriate transcript of TADG-12, 5 pmol and for the internal control β-tubulin, 0.2 mmol of dNTPs, 0.5 mCi of [α-$^{32}$P]dCTP, and 0.625 U of Taq polymerase in 1×buffer in a final volume of 25 ml. This mixture was subjected to 1 minute of denaturation at 95° C. followed by 30 cycles of denaturation for 30 seconds at 95° C., 30 seconds of annealing at 62° C., and 1 minute of extension at 72° C. with an additional 7 minutes of extension on the last cycle. The product was electrophoresed through a 2% agarose gel for separation, the gel was dried under vacuum and autoradiographed. The relative radioactivity of each band was determined by PhosphoImager from Molecular Dynamics.

Figure 7A:
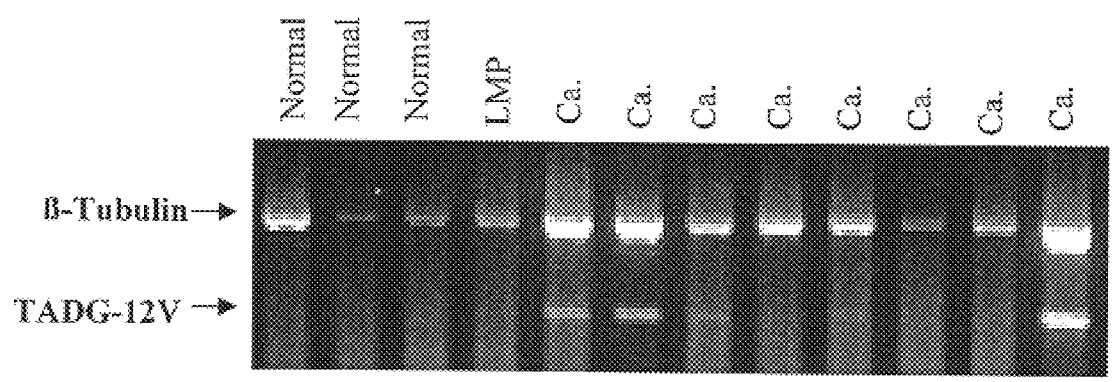
FIG. 7 shows PCR amplification of TADG-12-V (FIG. 7A) and TADG-12 (FIG. 7B) in relationship to an internal B-tubulin standard in normal and ovarian carcinoma.
Figure 7B:
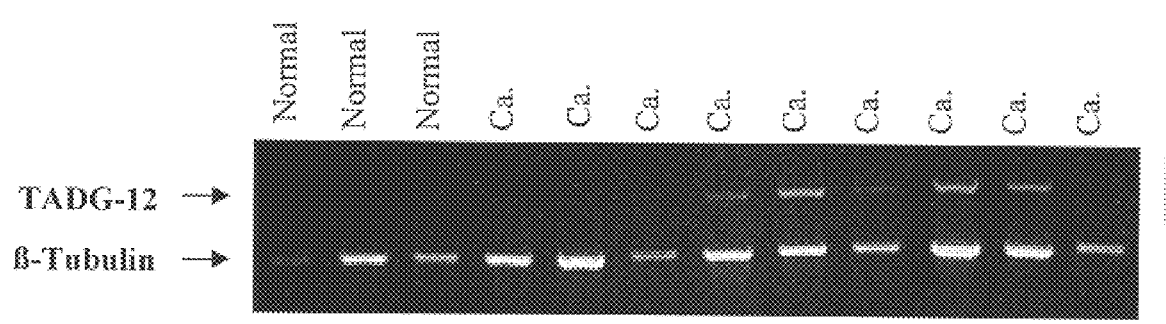

The results are shown in FIG. 7: a) TADG-12-V; b) TADG-12. Table I summarizes the expression of TADG-12 and TADG-12-V in normal and ovarian carcinomas. TADG-12 overall was expressed in about 45% of carcinomas (16/35). It is poorly expressed in mucinous tumors (1/10) but is relatively highly expressed in serous carcinomas (10/15) and endometrioid carcinomas (3/3). TADG-12-V is found in about 35% of ovarian carcinomas and is most prevalent in mucinous carcinomas (3/5).

TABLE I

Overexpression of TADG-12/TADG-12-V in Ovarian Carcinoma

| Histology Type | TADG-12 (%) | TADG-12-V (%) |
|---|---|---|
| Normal | 0 (%) | 0 (0%) |
| LMP-Serous | 3/6 (50%) | 0/5 (0%) |
| LMP-Mucinous | 0/4 (0%) | 0/3 (0%) |
| Carcinoma-Serous | 10/15 (67%) | 4/14 (29%) |
| Carcinoma-Mucinous | 1/6 (17%) | 3/5 (60%) |
| Carcinoma-Endometrioid | 3/3 (100%) | 1/3 (33%) |
| Carcinoma-Clear Cell | 0/3 (0%) | N.D. |

Overexpression = more than two standard deviations above the mean for normal ovary
LMP = low malignant potential tumor
N.D. = Not Done EXAMPLE 10
Immunohistochemical Analysis of TADG-12 in Ovarian Tumor Cells Immunohistochemical localization of TADG-12 antigen was examined using 3 normal ovaries, 1 serous low malignant potential (LMP) tumor, 1 mucinous LMP tumor, and 25 adenocarcinomas (9 serous adenocarcinomas, 7 mucinous adenocarcinomas, 1 clear cell carcinoma) plus 6 endometroid carcinomas. Formalin fixed and paraffin embedded sections, 4 μm thick, were cut and mounted on aminopropyltriethoxysilane treated slides. Slides were routinely deparaffinized with xylene and rehydrated with a series of ethanol washes. Nonenzymatic antigen retrieval was performed by processing using microwave heat treatment in 0.01 M sodium citrate buffer (pH 6.0).

Immunohistochemical staining was performed manually using the avidin-biotin peroxidase complex technique (Vectastain Elite ABC kit, Vector Laboratories). Anti-TADG-12 rabbit polyclonal antibody was generated by immunization with poly-lysine linked multiple Ag peptide derived from the TADG-12 carboxy protein-sequences. This indirect immunoperoxidase staining procedure was performed at room temperature. Endogenous peroxidase and nonspecific background staining were blocked by incubating slides with methanol in 0.3% $H_2O_2$ for 30 minutes. After washing with phosphate-buffered saline (PBS) for 10 minutes, sections were incubated with ABC reagent for 30 minutes. The final products were visualized by using AEC substrate system (DAKO Corporation), and sections were counter stained with Mayer hematoxylin for 20 seconds before mounting. Positive controls and negative controls were used for each section. Negative controls were performed by using normal rabbit serum instead of the primary antibody. All experiments were duplicated. The stained slides were examined microscopically by 3 observers. More than 10% of positive tumor cells was the criteria for a 1+ positive staining and more than 50% of positive tumor cells was the criteria for a 2+ positive staining.

Figure 8A:
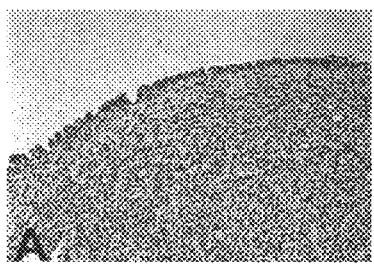
FIG. 8a shows a normal ovary with no staining.
Figure 8B:
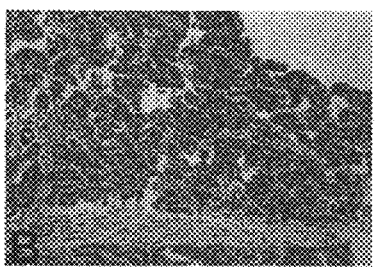
FIG. 8B shows an ovarian serous cystadenocarcinoma indicating positive staining in tumor cells.
Figure 8C:
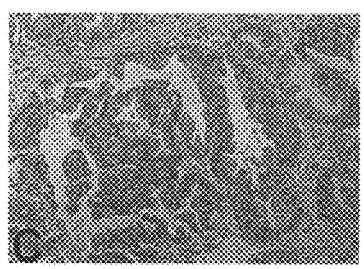
FIG. 8C shows a mucinous carcinoma with positive staining for TADG-12 staining and prognosis of 3 normal ovarian specimens and 29 ovarian tumors.

To further confirm the presence of the TADG-12 protein in ovarian tumor cells as opposed to its elaboration by supporting stromal or blood cells, both normal ovarian epithelia and ovarian tumor tissue were examined by immunohistochemistry using the polyclonal serum (described above). Representative results are illustrated in FIG. 8 which shows a normal ovary with no staining, an ovarian serous cystadenocarcinoma with TADG-12 positive tumor cells, and a mucinous carcinoma with positive staining for TADG-12.

The results of the immunohistochemical staining are summarized in Table II. Twenty-two of 29 ovarian tumors showed positive staining of TADG-12, whereas normal ovarian surface epithelium showed no expression of the TADG-12 antigen. Eight of 10 serous adenocarcinomas, 8 of 8 mucinous adenocarcinomas, 1 of 2 clear cell carcinomas, and 4 of 6 endometroid carcinomas showed positive staining.

TABLE II

| Case | Stage | Histology | Grade | LN* | TADG12 | Prognosis |
|---|---|---|---|---|---|---|
| 1 | | Normal ovary | | | 0− | |
| 2 | | Normal ovary | | | 0− | |
| 3 | | Normal ovary | | | 0− | |
| 4 | | Mucinous B | | ND | 0− | Alive |
| 5 | | Mucinous B | | ND | 1+ | Alive |
| 6 | 1a | Serous LMP | G1 | ND | 1+ | Alive |
| 7 | 1a | Mucinous LMP | G1 | ND | 1+ | Alive |
| 8 | 1a | Mucinous CA | G1 | ND | 1+ | Alive |
| 9 | 1a | Mucinous CA | G2 | ND | 1+ | Alive |
| 10 | 1a | Endometrioid CA | G1 | ND | 0− | Alive |
| 11 | 1c | Serous CA | G1 | N | 1+ | Alive |
| 12 | 1c | Mucinous CA | G1 | N | 1+ | Alive |
| 13 | 1c | Mucinous CA | G1 | N | 2+ | Alive |
| 14 | 1c | Clear cell CA | G2 | N | 0− | Alive |
| 15 | 1c | Clear cell CA | G2 | N | 0− | Alive |
| 16 | 2c | Serous CA | G3 | N | 2+ | Alive |
| 17 | 3a | Mucinous CA | G2 | N | 2+ | Alive |
| 18 | 3b | Serous CA | G1 | ND | 1+ | Alive |
| 19 | 3c | Serous CA | G1 | N | 0− | Dead |
| 20 | 3c | Serous CA | G3 | P | 1+ | Alive |
| 21 | 3c | Serous CA | G2 | P | 2+ | Alive |
| 22 | 3c | Serous CA | G1 | P | 2+ | Unknown |
| 23 | 3c | Serous CA | G3 | ND | 2+ | Alive |
| 24 | 3c | Serous CA | G2 | N | 0− | Dead |
| 25 | 3c | Mucinous CA | G1 | P | 2+ | Dead |
| 26 | 3c | Mucinous CA | G2 | ND | 1+ | Unknown |
| 27 | 3c | Mucinous CA | G2 | N | 1+ | Alive |
| 28 | 3c | Endometrioid CA | G1 | P | 1+ | Dead |
| 29 | 3c | Endometrioid CA | G2 | N | 0− | Alive |
| 30 | 3c | Endometrioid CA | G2 | P | 1+ | Dead |
| 31 | 3c | Endometrioid CA | G3 | P | 1+ | Alive |
| 32 | 3c | Clear Cell CA | G3 | P | 2+ | Dead |

LN* = Lymph Node: B = Benign; N = Negative; P = Positive; ND = Not Done

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. DNA encoding Tumor Antigen Derived Gene-12 protein (TADG-12), said protein having an amino acid sequence of SEQ ID No: 2, wherein said DNA is selected from the group consisting of:
   (a) isolated DNA which encodes a TADG-12 protein;
   (b) isolated DNA which hybridizes to isolated DNA of (a) above under high stringency conditions consisting of hybridization at 42° C. in the presence of about 50% formamide, a first wash at 65° C. with 2×SSC containing 1% SDS and a second wash at 65° C. with 0.1× SSC, wherein said DNA encodes a TADG-12 protein; and
   (c) isolated DNA differing from the isolated DNAs of (a) and (b) above in codon sequence due to the degeneracy of the genetic code, and which encodes a TADG-12 protein.

2. The DNA of claim 1, wherein said DNA has the sequence shown in SEQ ID No:1.

3. A vector comprising the DNA of claim 1 and regulatory elements necessary for expression of the DNA in a cell.

4. The vector of claim 3, wherein said DNA encodes a TADG-12 protein having the amino acid sequence shown in SEQ ID No:2.

5. A host cell transfected with the vector of claim 3, said vector expressing a TADG-12 protein.

6. The host cell of claim 5, wherein said cell is selected from group consisting of bacterial cells, mammalian cells, plant cells and insect cells.

7. The host cell of claim 6, wherein said bacterial cell is *E. coli*.

8. An antisense polynucleotide fully complementary to the DNA of claim 1.

* * * * *

SEQUENCE LISTING

<160> NUMBER OF SEQ ID NOS: 14

<210> SEQ ID NO 1
<211> LENGTH: 2416
<212> TYPE: DNA
<213> ORGANISM: Homo sapiens
<220> FEATURE:
<222> LOCATION: 144..1511
<223> OTHER INFORMATION: CDS

<400> SEQUENCE: 1

| | | | | | |
|---|---|---|---|---|---|
| cgggaaaggg | ctgtgtttat | gggaagccag | taacactgtg | gcctactatc | tcttccgtgg | 60 |
| tgccatctac | attttggga | ctcgggaatt | atgaggtaga | ggtggaggcg | gagccggatg | 120 |
| tcagaggtcc | tgaaatagtc | accatggggg | aaaatgatcc | gcctgctgtt | gaagccccct | 180 |
| tctcattccg | atcgctttt | ggccttgatg | atttgaaaat | aagtcctgtt | gcaccagatg | 240 |
| cagatgctgt | tgctgcacag | atcctgtcac | tgctgccatt | tgaagttttt | tcccaatcat | 300 |
| cgtcattggg | gatcattgca | ttgatattag | cactggccat | tggtctgggc | atccacttcg | 360 |
| actgctcagg | gaagtacaga | tgtcgctcat | cctttaagtg | tatcgagctg | ataactcgat | 420 |
| gtgacggagt | ctcggattgc | aaagacgggt | aggacgagta | ccgctgtgtc | cgggtgggtg | 480 |
| gtcagaatgc | cgtgctccag | gtgttcacag | ctgcttcgtg | gaagaccatg | tgctccgatg | 540 |
| actggaaggg | tcactacgca | aatgttgcct | gtgcccaact | gggtttccca | agctatgtga | 600 |
| gttcagataa | cctcagagtg | agctcgctgg | agggggcagtt | ccgggaggag | tttgtgtcca | 660 |
| tcgatcacct | cttgccagat | gacaaggtga | ctgcattaca | ccactcagta | tatgtgaggg | 720 |
| agggatgtgc | ctctggccac | gtggttacct | tgcagtgcac | agcctgtggt | catagaaggg | 780 |
| gctacagctc | acgcatcgtg | ggtggaaaca | tgtccttgct | ctcgcagtgg | ccctggcagg | 840 |
| ccagccttca | gttccagggc | taccacctgt | gcggggggctc | tgtcatcacg | ccctgtggga | 900 |
| tcatcactgc | tgcacactgt | gtttatgact | tgtacctccc | caagtcatgg | accatccagg | 960 |
| tgggtctagt | ttccctgttg | gacaatccag | ccccatccca | cttggtggag | aagattgttt | 1020 |
| accacagcaa | gtacaagcca | aagaggctgg | gcaatgacat | cgcccttatg | aagctggccg | 1080 |
| ggccactcac | gttcaatgaa | atgatccagc | ctgtgtgcct | gccaactct | gaagagaact | 1140 |
| tccccgatgg | aaaagtgtgc | tggacgtcag | gatgggggc | cacagaggat | ggaggtgacg | 1200 |
| cctcccctgt | cctgaaccac | gcggccgtcc | ctttgattc | caacaaagat | ctgcaaccac | 1260 |
| agggacgtgt | acgtggcat | catctccccc | tccatgctct | gcgcgggcta | cctgacgggt | 1320 |
| ggcgttggaa | cagctgccag | ggggacagcg | ggggccccct | ggtgtgtcaa | gagaggaggc | 1380 |
| tgtggaagtt | agtgggagcg | accagctttg | gcatcggctg | cgcagacgtg | aacaagcctg | 1440 |
| gggtgtacac | ccgtgtcacc | tccttcctgg | actggatcca | cgagcagatg | gagagagacc | 1500 |
| taaaaacctg | aagaggaagg | ggacaagtag | ccacctgagt | tcctgaggtg | atgaagacag | 1560 |
| cccgatcctc | ccctggactc | ccgtgtagga | acctgcacac | gagcagacac | ccttggagct | 1620 |
| ctgagttccg | gcaccagtag | cgggcccgaa | agaggcaccc | ttccatctga | ttccagcaca | 1680 |
| accttcaagc | tgctttttgt | tttttgtttt | tttgaggtgg | agtctcgctc | tgttgcccag | 1740 |
| gctggagtgc | agtggcgaaa | taccctgctc | actgcagcct | ccgcttccct | ggttcaagcg | 1800 |
| attctcttgc | ctcagcttcc | ccagtagctg | ggaccacagg | tgcccgccac | cacacccaac | 1860 |
| taattttgt | attttagta | gagacagggt | ttcaccatgt | tggccaggct | gctctcaaac | 1920 |

-continued

```
ccctgacctc aaatgatgtg cctgcttcag cctcccacag tgctgggatt acaggcatgg    1980
gccaccacgc ctagcctcac gctcctttct gatcttcact aagaacaaaa gaagcagcaa    2040
cttgcaaggg cggcctttcc cactggtcca tctggttttc tctccagggt cttgcaaaat    2100
tcctgacgag ataagcagtt atgtgacctc acgtgcaaag ccaccaacag ccactcagaa    2160
aagacgcacc agcccagaag tgcagaactg cagtcactgc acgttttcat ctttagggac    2220
cagaaccaaa cccacccttt ctacttccaa gacttatttt cacatgtggg gaggttaatc    2280
taggaatgac tcgtttaagg cctatttca tgatttcttt gtagcatttg gtgcttgacg    2340
tattattgtc ctttgattcc aaataatatg tttccttccc tcaaaaaaaa aaaaaaaaa    2400 aaaaaaaaaa aaaaa                                                     2416
```

<210> SEQ ID NO 2
<211> LENGTH: 455
<212> TYPE: PRT
<213> ORGANISM: Homo sapiens
<220> FEATURE:
<223> OTHER INFORMATION: Amino acid sequence of TADG-12 encoded by
      nucleotides 144 to 1511 of Sequence 1

<400> SEQUENCE: 2

```
Met Gly Glu Asn Asp Pro Pro Ala Val Glu Ala Pro Phe Ser Phe
              5                   10                  15

Arg Ser Leu Phe Gly Leu Asp Asp Leu Lys Ile Ser Pro Val Ala
             20                   25                  30

Pro Asp Ala Asp Ala Val Ala Ala Gln Ile Leu Ser Leu Leu Pro
             35                   40                  45

Phe Glu Val Phe Ser Gln Ser Ser Ser Leu Gly Ile Ile Ala Leu
             50                   55                  60

Ile Leu Ala Leu Ala Ile Gly Leu Gly Ile His Phe Asp Cys Ser
             65                   70                  75

Gly Lys Tyr Arg Cys Arg Ser Ser Phe Lys Cys Ile Glu Leu Ile
             80                   85                  90

Thr Arg Cys Asp Gly Val Ser Asp Cys Lys Asp Gly Glu Asp Glu
             95                  100                 105

Tyr Arg Cys Val Arg Val Gly Gly Gln Asn Ala Val Leu Gln Val
            110                  115                 120

Phe Thr Ala Ala Ser Trp Lys Thr Met Cys Ser Asp Asp Trp Lys
            125                  130                 135

Gly His Tyr Ala Asn Val Ala Cys Ala Gln Leu Gly Phe Pro Ser
            140                  145                 150

Tyr Val Ser Ser Asp Asn Leu Arg Val Ser Ser Leu Glu Gly Gln
            155                  160                 165

Phe Arg Glu Glu Phe Val Ser Ile Asp His Leu Leu Pro Asp Asp
            170                  175                 180

Lys Val Thr Ala Leu His His Ser Val Tyr Val Arg Glu Gly Cys
            185                  190                 195

Ala Ser Gly His Val Val Thr Leu Gln Cys Thr Ala Cys Gly His
            200                  205                 210

Arg Arg Gly Tyr Ser Ser Arg Ile Val Gly Gly Asn Met Ser Leu
            215                  220                 225

Leu Ser Gln Trp Pro Trp Gln Ala Ser Leu Gln Phe Gln Gly Tyr
            230                  235                 240

His Leu Cys Gly Gly Ser Val Ile Thr Pro Leu Trp Ile Ile Thr
            245                  250                 255
```

```
Ala Ala His Cys Val Tyr Asp Leu Tyr Leu Pro Lys Ser Trp Thr
            260                 265                 270

Ile Gln Val Gly Leu Val Ser Leu Leu Asp Asn Pro Ala Pro Ser
        275                 280                 285

His Leu Val Glu Lys Ile Val Tyr His Ser Lys Tyr Lys Pro Lys
        290                 295                 300

Arg Leu Gly Asn Asp Ile Ala Leu Met Lys Leu Ala Gly Pro Leu
        305                 310                 315

Thr Phe Asn Glu Met Ile Gln Pro Val Cys Leu Pro Asn Ser Glu
        320                 325                 330

Glu Asn Phe Pro Asp Gly Lys Val Cys Trp Thr Ser Gly Trp Gly
        335                 340                 345

Ala Thr Glu Asp Gly Gly Asp Ala Ser Pro Val Leu Asn His Ala
        350                 355                 360

Ala Val Pro Leu Ile Ser Asn Lys Asp Leu Gln Pro Gln Gly Arg
        365                 370                 375

Val Arg Trp His His Leu Pro Leu His Ala Leu Arg Gly Leu Pro
        380                 385                 390

Asp Gly Trp Arg Trp Asn Ser Cys Gln Gly Asp Ser Gly Gly Pro
        395                 400                 405

Leu Val Cys Gln Glu Arg Arg Leu Trp Lys Leu Val Gly Ala Thr
        410                 415                 420

Ser Phe Gly Ile Gly Cys Ala Asp Val Asn Lys Pro Gly Val Tyr
        425                 430                 435

Thr Arg Val Thr Ser Phe Leu Asp Trp Ile His Glu Gln Met Glu
        440                 445                 450

Arg Asp Leu Lys Thr
        455

<210> SEQ ID NO 3
<211> LENGTH: 328
<212> TYPE: DNA
<213> ORGANISM: Homo sapiens
<220> FEATURE:
<223> OTHER INFORMATION: TADG-12 sequence variant containing 133 base
      pair insertion (32..162)

<400> SEQUENCE: 3
gggtggtgac ggcggcgcac tgtgtttatg agattgtagc tcctagagaa agggcagaca      60
gaagaggaag gaagctcctg tgctggagga aacccacaaa aatgaaagga cctagacctt     120
cccatagcta attccagtgg accatgttat ggcagataca ggcttgtacc tccccaagtc     180
atggaccatc caggtgggtc tagtttccct gttggacaat ccagccccat cccacttggt     240
ggagaagatt gtctaccaca gcaagtacaa gccaaagagg ctgggcaacg acatcgccct     300
cctaatcact agtgcggccg cctgcagg                                        328

<210> SEQ ID NO 4
<211> LENGTH: 42
<212> TYPE: PRT
<213> ORGANISM: Homo sapiens
<220> FEATURE:
<223> OTHER INFORMATION: Amino acid sequence encoded by of TADG-12
      variant with 133 b.p. insertion. Amino acids from 11 to the
      premature truncation after amino acid 42 are novel

<400> SEQUENCE: 4

Val Val Thr Ala Ala His Cys Val Tyr Glu Ile Val Ala Pro Arg
```

```
                    5                  10                 15
Glu Arg Ala Asp Arg Arg Gly Arg Lys Leu Leu Cys Trp Arg Lys
                   20                  25                 30

Pro Thr Lys Met Lys Gly Pro Arg Pro Ser His Ser
                   35                  40

<210> SEQ ID NO 5
<211> LENGTH: 154
<212> TYPE: PRT
<213> ORGANISM: Unknown
<220> FEATURE:
<223> OTHER INFORMATION: Serine protease catalytic domain of protease M
      (Prom) homologous to similar domain in TADG-12.

<400> SEQUENCE: 5

Cys Gly Gly Val Leu Ile His Pro Leu Trp Val Leu Thr Ala Ala
                    5                  10                 15

His Cys Lys Lys Pro Asn Leu Gln Val Phe Leu Gly Lys His Asn
                   20                  25                 30

Leu Arg Gln Arg Glu Ser Ser Gln Glu Gln Ser Ser Val Val Arg
                   35                  40                 45

Ala Val Ile His Pro Asp Tyr Asp Ala Ala Ser His Asp Gln Asp
                   50                  55                 60

Ile Met Leu Leu Arg Leu Ala Arg Pro Ala Lys Leu Ser Glu Leu
                   65                  70                 75

Ile Gln Pro Leu Pro Leu Glu Arg Asp Cys Ser Ala Asn Thr Thr
                   80                  85                 90

Ser Cys His Ile Leu Gly Trp Gly Lys Thr Ala Asp Gly Asp Phe
                   95                 100                105

Pro Asp Thr Ile Gln Cys Ala Tyr Ile His Leu Val Ser Arg Glu
                  110                 115                120

Glu Cys Glu His Ala Tyr Pro Gly Gln Ile Thr Gln Asn Met Leu
                  125                 130                135

Cys Ala Gly Asp Glu Lys Tyr Gly Lys Asp Ser Cys Gln Gly Asp
                  140                 145                150

Ser Gly Gly Pro

<210> SEQ ID NO 6
<211> LENGTH: 156
<212> TYPE: PRT
<213> ORGANISM: Unknown
<220> FEATURE:
<223> OTHER INFORMATION: Serine protease catalytic domain of
      trypsinogen 1 (Try1) homologous to similar domain in TADG-12

<400> SEQUENCE: 6

Cys Gly Gly Ser Leu Ile Asn Glu Gln Trp Val Val Ser Ala Gly
                    5                  10                 15

His Cys Tyr Lys Ser Arg Ile Gln Val Arg Leu Gly Glu His Asn
                   20                  25                 30

Ile Glu Val Leu Glu Gly Asn Glu Gln Phe Ile Asn Ala Ala Lys
                   35                  40                 45

Ile Ile Arg His Pro Gln Tyr Asp Arg Lys Thr Leu Asn Asn Asp
                   50                  55                 60

Ile Met Leu Ile Lys Leu Ser Ser Arg Ala Val Ile Asn Ala Arg
                   65                  70                 75

Val Ser Thr Ile Ser Leu Pro Thr Ala Pro Pro Ala Thr Gly Thr
                   80                  85                 90
```

```
Lys Cys Leu Ile Ser Gly Trp Gly Asn Thr Ala Ser Ser Gly Ala
                95                 100                 105

Asp Tyr Pro Asp Glu Leu Gln Cys Leu Asp Ala Pro Val Leu Ser
                110                 115                 120

Gln Ala Lys Cys Glu Ala Ser Tyr Pro Gly Lys Ile Thr Ser Asn
                125                 130                 135

Met Phe Cys Val Gly Phe Leu Glu Gly Lys Asp Ser Cys Gln
                140                 145                 150

Gly Asp Ser Gly Gly Pro
                155

<210> SEQ ID NO 7
<211> LENGTH: 154
<212> TYPE: PRT
<213> ORGANISM: Unknown
<220> FEATURE:
<223> OTHER INFORMATION: Serine protease catalytic domain of stratum
      corneum chymotryptic enzyme (Scce) homologous to similar
      domain in TADG-12

<400> SEQUENCE: 7

Cys Gly Gly Val Leu Val Asn Glu Arg Trp Val Leu Thr Ala Ala
                 5                  10                  15

His Cys Lys Met Asn Glu Tyr Thr Val His Leu Gly Ser Asp Thr
                20                  25                  30

Leu Gly Asp Arg Arg Ala Gln Arg Ile Lys Ala Ser Lys Ser Phe
                35                  40                  45

Arg His Pro Gly Tyr Ser Thr Gln Thr His Val Asn Asp Leu Met
                50                  55                  60

Leu Val Lys Leu Asn Ser Gln Ala Arg Leu Ser Ser Met Val Lys
                65                  70                  75

Lys Val Arg Leu Pro Ser Arg Cys Glu Pro Pro Gly Thr Thr Cys
                80                  85                  90

Thr Val Ser Gly Trp Gly Thr Thr Thr Ser Pro Asp Val Thr Phe
                95                 100                 105

Pro Ser Asp Leu Met Cys Val Asp Val Lys Leu Ile Ser Pro Gln
                110                 115                 120

Asp Cys Thr Lys Val Tyr Lys Asp Leu Leu Glu Asn Ser Met Leu
                125                 130                 135

Cys Ala Gly Ile Pro Asp Ser Lys Lys Asn Ala Cys Asn Gly Asp
                140                 145                 150

Ser Gly Gly Pro

<210> SEQ ID NO 8
<211> LENGTH: 161
<212> TYPE: PRT
<213> ORGANISM: Unknown
<220> FEATURE:
<223> OTHER INFORMATION: Serine protease catalytic domain of hepsin
      (Heps) homologous to similar domain in TADG-12

<400> SEQUENCE: 8

Cys Gly Gly Ser Leu Leu Ser Gly Asp Trp Val Leu Thr Ala Ala
                 5                  10                  15

His Cys Phe Pro Glu Arg Asn Arg Val Leu Ser Arg Trp Arg Val
                20                  25                  30

Phe Ala Gly Ala Val Ala Gln Ala Ser Pro His Gly Leu Gln Leu
                35                  40                  45
```

```
Gly Val Gln Ala Val Phe Arg His Pro Gly Tyr Ser Thr Gln Thr
             50                  55                  60

His Val Asn Asp Leu Met Leu Val Lys Leu Asn Ser Gln Ala Arg
             65                  70                  75

Leu Ser Ser Met Val Lys Lys Val Arg Leu Pro Ser Arg Cys Glu
             80                  85                  90

Pro Pro Gly Lys Ile Cys Thr Val Thr Gly Trp Gly Asn Thr Gln
             95                 100                 105

Tyr Tyr Gly Gln Gln Ala Gly Val Leu Gln Glu Ala Arg Val Pro
            110                 115                 120

Ile Ile Ser Asn Asp Val Cys Asn Gly Ala Asp Phe Tyr Gly Asn
            125                 130                 135

Gln Ile Lys Pro Lys Met Phe Cys Ala Gly Tyr Pro Glu Gly Gly
            140                 145                 150

Ile Asp Ala Cys Gln Gly Asp Ser Gly Gly Pro
            155                 160
```

```
<210> SEQ ID NO 9
<211> LENGTH: 20
<212> TYPE: DNA
<213> ORGANISM: Artificial Sequence
<220> FEATURE:
<221> NAME/KEY: primer_bind
<223> OTHER INFORMATION: Sense nucleotide for the conserved histidine
      of the of the catalytic triad (His-Asp-Ser) essential for
      serine protease activity; n = inosine at nucleotides
      3, 6, 9, 12, 15, and 18.

<400> SEQUENCE: 9
tgggtngtna cngcngcnca                                                20

<210> SEQ ID NO 10
<211> LENGTH: 20
<212> TYPE: DNA
<213> ORGANISM: Artificial Sequence
<220> FEATURE:
<221> NAME/KEY: primer_bind
<223> OTHER INFORMATION: Antisense oligonucleotide for the conserved
      aspartic acid of the catalytic triad (His-Asp-Ser)
      essential for serine protease activity; n =
      inosine at nucleotides 3, 6, 9, 12, 15, and 18

<400> SEQUENCE: 10
arnarngcna tntcnttncc                                                20

<210> SEQ ID NO 11
<211> LENGTH: 20
<212> TYPE: DNA
<213> ORGANISM: Artificial Sequence
<220> FEATURE:
<221> NAME/KEY: primer_bind
<223> OTHER INFORMATION: T12-V Sense: specific primer for variant
      TADG-12 transcript

<400> SEQUENCE: 11
tccaggtggg tctagtttcc                                                20

<210> SEQ ID NO 12
<211> LENGTH: 20
<212> TYPE: DNA
<213> ORGANISM: Artificial Sequence
<220> FEATURE:
<221> NAME/KEY: primer_bind
<222> LOCATION: 1-20
```

```
<223> OTHER INFORMATION: T12-V Anti-sense: specific primer for variant
      TADG-12 transcript

<400> SEQUENCE: 12
ctctttggct tgtacttgct                                                    20

<210> SEQ ID NO 13
<211> LENGTH: 20
<212> TYPE: DNA
<213> ORGANISM: Artificial Sequence
<220> FEATURE:
<221> NAME/KEY: primer_bind
<223> OTHER INFORMATION: T12 Sense: specific primer for standard TADG-12
      transcript

<400> SEQUENCE: 13
gaaacatgtc cttgctctcg                                                    20

<210> SEQ ID NO 14
<211> LENGTH: 20
<212> TYPE: DNA
<213> ORGANISM: Artificial Sequence
<220> FEATURE:
<221> NAME/KEY: primer_bind
<222> LOCATION: 1-20
<223> OTHER INFORMATION: T12 Anti-sense: specific primer for standard
      TADG-12 transcript

<400> SEQUENCE: 14
actaacttcc acagcctcct                                                    20
```